US009999663B2

United States Patent
Bueno Ramirez et al.

(10) Patent No.: US 9,999,663 B2
(45) Date of Patent: Jun. 19, 2018

(54) IMMUNOGENIC FORMULATION CONTAINING RECOMBINANT LIVE BCG THAT EXPRESS ANTIGENS OF METAPNEUMOVIRUS (HMPV), IN A SUSPENSION PREPARED FROM A LYOPHILISATE, WITHOUT REQUIRING AN ADJUVANT, SUITABLE FOR PHARMACEUTICAL USE

(71) Applicant: PONTIFICIA UNIVERSIDAD CATOLICA DE CHILE, Santiago (CL)

(72) Inventors: Susan Marcela Bueno Ramirez, Santiago (CL); Alexis Mikes Kalergis Parra, Santiago (CL); Christian Palavecino Beaumont, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 24 days.

(21) Appl. No.: 15/025,976

(22) PCT Filed: Sep. 30, 2014

(86) PCT No.: PCT/IB2014/064963
§ 371 (c)(1),
(2) Date: Mar. 30, 2016

(87) PCT Pub. No.: WO2015/049633
PCT Pub. Date: Apr. 9, 2015

(65) Prior Publication Data
US 2016/0220662 A1    Aug. 4, 2016

(30) Foreign Application Priority Data

Oct. 1, 2013 (CL) .......................... CL2013-02829

(51) Int. Cl.
*A61K 39/155* (2006.01)
*A61K 39/12* (2006.01)
*C12N 7/00* (2006.01)
*A61K 39/00* (2006.01)

(52) U.S. Cl.
CPC ............ *A61K 39/155* (2013.01); *A61K 39/12* (2013.01); *C12N 7/00* (2013.01); *A61K 2039/522* (2013.01); *A61K 2039/523* (2013.01); *A61K 2039/54* (2013.01); *A61K 2039/55594* (2013.01); *C12N 2760/18334* (2013.01); *C12N 2760/18371* (2013.01); *C12N 2760/18534* (2013.01)

(58) Field of Classification Search
None
See application file for complete search history.

(56) References Cited

FOREIGN PATENT DOCUMENTS

| ES | 2393468 T3 | 12/2012 |
|---|---|---|
| WO | 2007120120 A2 | 10/2007 |
| WO | 2008137981 A1 | 11/2008 |

OTHER PUBLICATIONS

Bowie et al. (Science, 1990, 247:1306-1310).*
Greenspan et al. (Nature Biotechnology 7: 936-937, 1999).*
Pham QN, et al; Chimeric recombinant human metapneumoviruses with the nucleoprotein or . . . ; Journal of Virology; 2005; vol. 79 (24); pp. 15114-15122.
International Search Report dated Feb. 20, 2015 for PCT/IB2014/064963 and English translation.

* cited by examiner

*Primary Examiner* — Brian Gangle
(74) *Attorney, Agent, or Firm* — Lucas & Mercanti, LLP (57) ABSTRACT

The present invention relates to an immunogenic formulation to be used in mammals against human Metapneumovirus (hMPV), consisting of a lyophilisate of $1 \times 10^9$ ufc/ml of recombinant BCG that expresses the viral protein P of hMPV (of genogroups A1, A2, B1 and B2). The vaccine is derived from the full or partial product of the P gene of hMPV, capable of being used, stabilised and administered in solution without requiring adjuvants. The preparation can also contain combinations of the aforementioned formulations. The formulation is stabilised by means of lyophilisation (conservation range of between 4° C. and 8° C.) in order to be subsequently reconstituted in an adjuvant-free saline solution prior to use.

13 Claims, 5 Drawing Sheets

SEQUENCE LISTING

```
<160> NUMBER OF SEQ ID NOS: 4

<210> SEQ ID NO 1
<211> LENGTH: 26
<212> TYPE: DNA
<213> ORGANISM: Human Metapneumovirus

<400> SEQUENCE: 1
gaattcatgt cattccctga aggaaa                                    26

<210> SEQ ID NO 2
<211> LENGTH: 26
<212> TYPE: DNA
<213> ORGANISM: Human Metapneumovirus

<400> SEQUENCE: 2
gaattcctac ataattaact ggtaaa                                    26

<210> SEQ ID NO 3
<211> LENGTH: 897
<212> TYPE: DNA
<213> ORGANISM: Human Metapneumovirus

<400> SEQUENCE: 3
gaattcatgt cattccctga aggaaaagat attcttttca tgggtaatga agcggcaaaa    60
```

```
ttggcagaag ctttccaaaa atcattaaga aaacctagtc ataaaagatc tcaatctatt    120
ataggagaaa aagtgaacac tgtatctgaa acattggaat tacctactat cagtagacct    180
accaaaccga ccatattgtc agagccgaag ttagcatgga cagacaaagg tggggcaatc    240
aaaactgaag caaagcaaac aatcaaagtt atggatccta ttgaagaaga agagtttact    300
gagaaaaggg tgctgccctc cagtgatggg aaaactcctg cagaaaagaa gttgaaacca    360
tcaaccaata ctaaaaagaa ggtctcattt acaccaaatg aaccaggaaa atacacaaag    420
ttggagaaag atgctctaga cttgctttca gacaatgaag aagaagatgc agaatcctca    480
atcttaacct tcgaagaaag agatacttca tcattaagca ttgaagccag actagaatcg    540
attgaggaga aattaagcat gatattaggg ctattaagaa cactcaacat tgctacagca    600
ggacccacag cagcaagaga tgggatcaga gatgcaatga ttggcataag ggaggaacta    660
atagcagaca taataaaaga agccaaggga aaagcagcag aaatgatgga agaagaaatg    720
aaccagcgga caaaaatagg aaacggtagt gtaaaattaa ctgaaaaggc aaaggagctc    780
aacaaaattg ttgaagacga gagcacaagt ggtgaatccg aagaagaaga agaactaaaa    840
gacacacagg aaaataatca agaagatgac atttaccagt taattatgta ggaattc       897

<210> SEQ ID NO 4
<211> LENGTH: 49
<212> TYPE: PRT
<213> ORGANISM: human respiratory syncytial virus

<400> SEQUENCE: 4

His Met Lys Lys Arg Gly Leu Thr Val Ala Val Ala Gly Ala Ala Ile
1               5                   10                  15

Leu Val Ala Gly Leu Ser Gly Cys Ser Ser Asn Lys Ser Thr Thr Gly
            20                  25                  30

Ser Gly Glu Thr Thr Thr Thr Ala Ala Gly Thr Thr Ala Ser Pro Gly
        35                  40                  45

Gly
```

IMMUNOGENIC FORMULATION CONTAINING RECOMBINANT LIVE BCG THAT EXPRESS ANTIGENS OF METAPNEUMOVIRUS (HMPV), IN A SUSPENSION PREPARED FROM A LYOPHILISATE, WITHOUT REQUIRING AN ADJUVANT, SUITABLE FOR PHARMACEUTICAL USE

CROSS REFERENCE TO RELATED APPLICATION

This Application is a 371 of PCT/IB2014/064963 filed on Sep. 30, 2014, which, in turn, claimed the priority of Chilean Patent Application No. CL2013-02829 filed on Oct. 1, 2013, both applications are incorporated herein by reference.

FIELD OF THE INVENTION

The present invention relates to the fields of immunology and biotechnology, and is specifically directed to an immunogenic formulation based on a recombinant attenuated bacteria to be used to prepare a vaccine against human metapneumovirus (hMPV). This formulation contains the recombinant *Bacillus* Calmette-Guérin (BCG) expressing the antigenic peptide P-protein from hMPV virus.

BACKGROUND OF THE INVENTION

The human metapneumovirus (hMPV, hereinafter) is the etiologic agent of a high percentage of hospitalizations and morbidity associated with acute respiratory infections of the upper and lower respiratory tracts, especially in infants, elderly and immunocompromised individuals. Infection with this virus is associated with a wide range of conditions, being bronchiolitis and pneumonia the conditions with a higher socio-economic impact. Additionally, it have been associated with gastroenteritis, and keratoconjunctivitis. Calvo et al. (2008) demonstrated in a 3 years period study that cumulative incidence of acute respiratory infections caused by respiratory viruses RSV, ADV and hMPV accounted for 64.5% of hospital admissions of children younger than 2 years, being the incidence for each virus 35.4%, 19.3% and 9.8%, respectively. One interesting feature that hMPV shares with the other high incidence respiratory viruses is the production of repeated infections throughout childhood, a phenomenon possibly associated with a failure in the establishment of a protective immune response to the first infection during early months of life. This latest phenomenon motivates the urgent need for public health systems to have new prototype of vaccines with the ability to control annual outbreaks of respiratory infections, thereby allowing relieve congestion in healthcare institutions and ultimately the socio-economic impact associated with these infections. To date, there are no studies about the specific economic impact of hMPV infection, however, the incidence of hospitalization for hMPV has been estimated in ⅓ of the incidence of hospitalization for human respiratory syncytial virus (hRSV). Studies conducted in developed countries estimate individual cost of hRSV infection about 3,000 euros ($1.86 million Chilean pesos) with an upper limit of up to 8,400 euros ($5.2 million Chilean pesos). The costs associated to individual hospitalization are approximate and based on a pathological process of similar characteristics that requires hospitalization.

The hMPV virus is classified in the family Paramyxoviridae subfamily Pneumovirinae, the same family in which hRSV is classified, although each one is grouped within the Metapneumovirus and *Pneumovirus* genus, respectively. HMPV genome comprises a non-segmented, single-stranded, negative-sense ribonucleic acid (ssRNA), so that the viral proteins are arranged in a 3' to 5' direction (with respect to their sequence) as follows: N, P, M, F, M2 (ORF1 and 2), SH, G and L. Five of these proteins are responsible for packaging the genetic material and defining the structure of the viral particle, corresponding to the nucleocapsid protein N and the matrix protein M, together with transmembrane glycoproteins F, G and SH, respectively. The other four proteins, M2-1, M2-2, P and L, are involved in viral replication and transcription. There are two subtypes of hMPV, classified as A and B relative to two antigenic groups based on sequence differences primarily in proteins F and G. Although these proteins have some degree of difference, there is a high identity compared to other proteins encoded by the viral genome. The development of vaccines against respiratory viruses began in the 1960s with the first prototype of hRSV vaccine based on formalin-inactivated virus (hRSV-FI), which had significant adverse effects that prevented its use in immunization programs. The intramuscular formulation together with aluminum hydroxide adjuvant produced in vaccinated infants more severe symptoms than those in infected individuals not vaccinated. This effect was associated with a hyper-responsiveness of the immune response to infection, characterized by a large parenchymal infiltration of polymorphonuclear cells, eosinophils and neutrophils and a high titer of complement-fixing antibodies.

For human metapneumovirus (hMPV) only few vaccines have been developed and so far none has had a satisfactory result. A prototype using the same previous design of formalin-inactivated virus (hMPV-FI), also produced inflammatory hyper-responsiveness symptoms with similar characteristics to that produced by the vaccine against hRSV in a *Sigmodon hispidus* infection model (Yim et al., 2007). In contrast with the hyper-responsiveness processes observed for hSRV, partial elimination of the virus from the respiratory system was demonstrated. The disease observed in mice and *Sigmodon hispidus* exposed to hSRV-Fl was associated with an immunopathological response based on Th2-type antibodies and an exaggerated activation of NF-κB. Increased NF-κB transcriptional activity further relates to the secretion of pro-inflammatory cytokines such as IL-8. Furthermore, the hyper-responsiveness of lung tissue after hMPV infection has been associated with immune responses characterized by presence of IFN-γ and IL-4 in bronchoalveolar lavage and detection of IgG1 and IgG2a neutralizing antibodies in sick mice serum, strongly suggesting that chronic inflammation observed is due either to pathological responses of Th1 and Th2 type or an insufficient response based on Th1-type cells accompanied by a pathological Th2 response. As for the latter assumption, some authors have proposed that an increased Th1 response could also exacerbate the disease.

These facts emphasize the importance of establishing a balanced and efficient immune response able to limit the progress of the inflammatory process and, in turn, induce the proper clearance of these viruses from infected tissues.

Because the respiratory disease caused by hMPV is similar to what was previously observed with hSRV, which has been associated with a failure in the induction of cellular immunity, it is necessary to generate a prototype vaccine which is a good inducer of CD8+ cytotoxic T and CD4+ helper T cells, both IFN-γ producers. Recent experimental approaches have focused their efforts on developing vaccines only towards one viral species, using different techniques of molecular genetics and immunology. It is important to mention that these studies have used a limited number of proteins or protein subunits as antigens for each virus of interest. For hSRV, some of them have been based on the use of individual viral proteins, such as whole subunits or fragments of F or G proteins, or a mixture thereof in murine and non-human primate models of infection. Some vaccine prototypes against hSRV have been used in phase I and II clinical trials, but the results have not shown a long-term protective ability, and vaccines are far from suitable for extensive use in the prophylaxis of infection (Denis et al., 2005; Karron et al., 2005).

Attenuated hMPV strains have been developed by eliminating genes that have been suggested are related to viral pathogenicity. HMPV strains lacking of genes encoding for SH, G, and, M2-1 and M2-2 proteins have been proposed as vaccine candidates (Biacchesi et al., 2005). These candidates have showed good results in animal models but have not yet been studied in humans. Although this alternative is viable, it is very expensive as it requires the production of virus in cell cultures approved for human use. Another source of vaccine is the overexpression of viral proteins by heterologous systems, such as hMPV F-protein coupled with adjuvants for generate neutralizing antibodies, but the disadvantage of this option is that provides immunity for a very short period of time (Herfst et al., 2008a).

There are no clinical studies of vaccine candidates against hMPV, because the development of prototypes capable of generating protective immunity has failed. To date, prototypes evaluated in animal models generate Th2-type antibody-based immunity, which are not long-term or effective preventing infection. Animals vaccinated with these prototypes generate neutralizing antibodies in vitro, but they are not protected against infection or the clinical symptoms of disease induced by hMPV infection in mice (Cseke et al., 2007) or macaques (Herfst et al., 2008b) are reduced. The antibody-based immunity is not efficient neutralizing virus in vivo. Antibodies capable of neutralizing hMPV in vitro, are not able to prevent infection or disease caused by hMPV, when used as therapy via passive immunization (Hamelin et al., 2008). Moreover, it has been observed that the resolution of viral symptoms requires the participation of Th1-type cell-based immune response. It was shown that the resolution of the viral condition and clearance of viral particles is dependent on the activation of CD4+ and CD8+ lymphocytes, even though the activity of these is also responsible for the immunopathology of disease (Kolli et al., 2008). More recently it has been found that the primary effectors of viral symptoms resolution are CD8+-type cytotoxic cells, although CD4+ helper T lymphocytes have a regulatory involvement. Thus, a balanced immune response of Th1-type cells is needed to produce the resolution of viral symptoms without causing inflammatory hyper-responsiveness. In summary, currently there is no vaccine against human metapneumovirus (hMPV) able to give effective protection and with no major side effects, in fact, there are no commercial vaccines available against this virus.

Surprisingly the inventors have found that the use of a recombinant *Mycobacterium* strain expressing P-protein from human Metapneumovirus allows to generate a protective immunity against infection produced by respiratory Metapneumovirus virus without causing unacceptable side effects, such as inflammatory hyper-responsiveness in airways. This invention solves a technical problem that remained unsolved in the prior art, consisting of an immunogenic formulation that provides protection against infections by hMPV and not generate inflammatory hyper-responsiveness.

DESCRIPTION OF THE FIGURES

Figure 1:
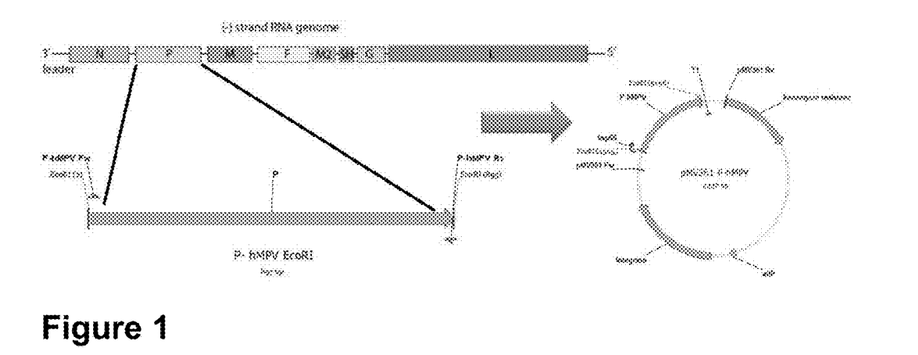
FIG. 1A shows the hMPV genome, and the gene encoding for P-protein.
FIG. 1B shows pMV361-P-hMPV vector incorporating said gene encoding for P-protein.

FIG. 1: Generation of pMV361-P-hMPV Construct. From metapneumovirus RNA reverse transcription was performed with universal primers and then amplified with P-hMPV-Fw and P-hMPV-Rv primers from the open reading frame of P gene. EcoRI sites at both ends were incorporated to the amplification product and then it was inserted into the EcoRI site of pMV361 mycobacterial vector to generate the construct vector pMV361-P-hMPV. FIG. 1A shows the hMPV genome, and the gene encoding for P-protein, and FIG. 1B shows pMV361-P-hMPV vector incorporating said gene encoding for P-protein.

Figure 2:
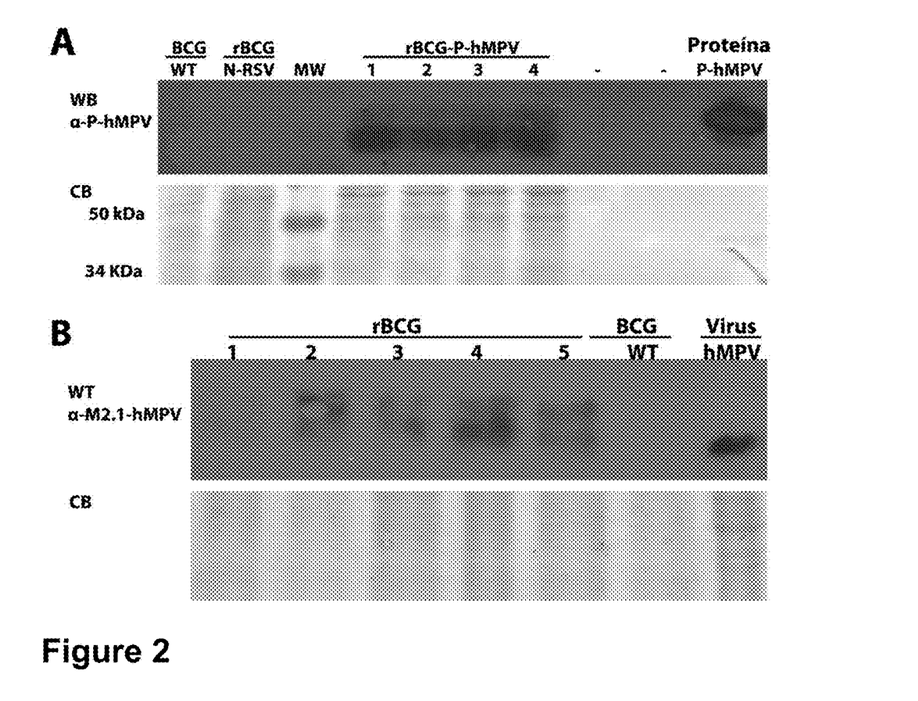
FIG. 2A shows a Western Blot using monoclonal anti-hMPV P-protein antibodies.
FIG. 2B shows a Western Blot using monoclonal anti-hMPV M2.1 protein antibodies.

FIG. 2. Expression of P-Protein or M2.1 Protein from hMPV by Recombinants Strains of *Mycobacterium* BCG. The *Mycobacterium* BCG Danish strain was electrotransformed with plasmid pMV361-P-hMPV and was selected on Middlebrook 7H10 agar medium supplemented with oleic acid, albumin, dextrose and catalase containing 20 μg/ml of kanamycin. SDS-PAGE (CB) electrophoresis and Western blot (WB) were performed using monoclonal anti-hMPV P-protein antibodies (WB). FIG. 2A: Western Blot using monoclonal anti-hMPV P-protein antibodies and FIG. 2B: Western Blot using monoclonal anti-hMPV M2.1 protein antibodies. In SDS-PAGE, 25 μg of total P-protein prepared from four clones of rBCG-P-hMPV (FIG. 2A) or five clones from rBCG-M2.1-hMPV (FIG. 2B) were loaded. As a positive control 5 ng of recombinant hMPV P-protein or 25 μg of inactivated hMPV, as appropriate, were loaded. As negative control, total protein from the wild type strain of BCG was loaded and in the case of rBCG-P-MPV a BCG recombinant for N gene from SRV (N-5 strain) was also loaded. It can be appreciated that all the clones analyzed express the cloned plasmid protein, either, P-protein, FIG. 2A, or M2.1 protein, FIG. 2B.

Figure 3:
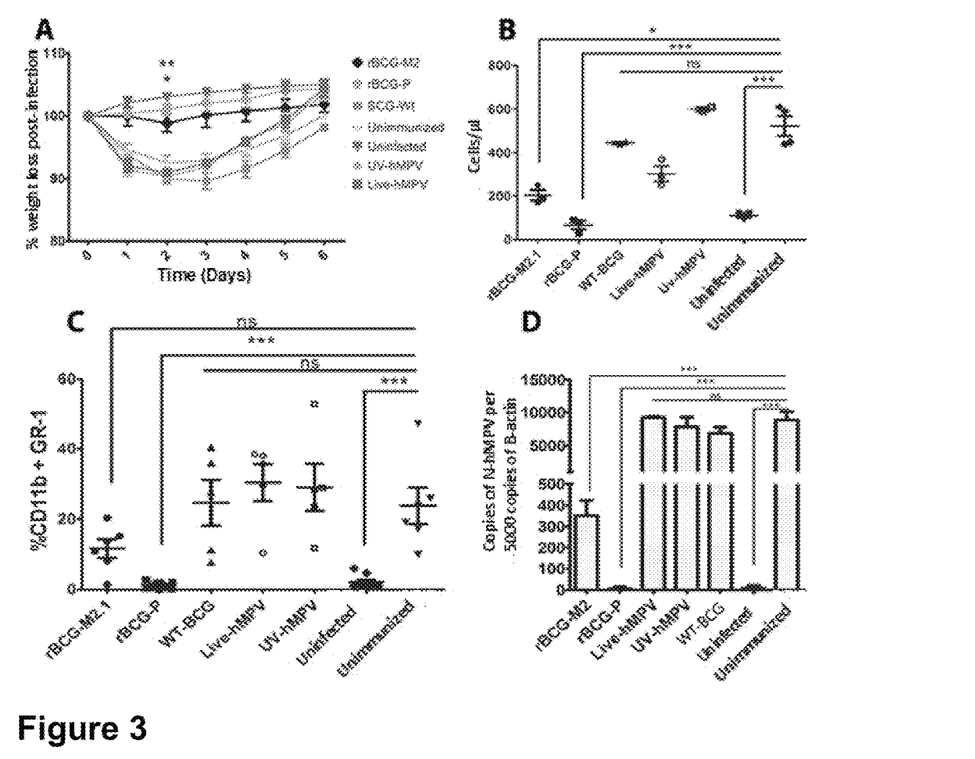
FIG. 3A shows a graphic representation of weight loss for each group of animals following infection.
FIG. 3B shows the total number of cells infiltrating the airways.
FIG. 3C shows the percentage of cells that reacted positively to double staining with CD11b and Gr1 in BAL.
FIG. 3D shows the determination of hMPV RNA in lungs of infected mice by quantitative PCR.

FIG. 3. Immunization with Recombinant rBCG-P-hMPV Protects Against Infection with hMPV. Groups of 4-8 weeks BALB/c mice received a subdermal dose of $1 \times 10^6$ colony forming units (CFU) of rBCG-M2.1-hMPV, rBCG-P-hMPV or WT-BCG (wild-type) and were also vaccinated with $1 \times 10^6$ plaque forming units (PFU) of live virus (Live-hMPV) or UV-inactivated virus (UV-hMPV). Then all groups were intranasally infected with $1 \times 10^6$ PFU of hMPV. As control group unvaccinated animals and one other group of uninfected animals were included. During six days after infection the weight of the animals was recorded and were sacrificed at the end of each experiment and a bronchoalveolar lavage (BAL) and lungs were obtained from each one. The symbols represent individual animals and the horizontal bar is the mean. (FIG. 3 A) Graphic representation of weight loss for each group of animals following infection. (FIG. 3 B) Total of cells infiltrating the airways. (FIG. 3 C) Percentage of cells that reacted positively to double staining with CD11b and Gr1 in BAL. (FIG. 3 D) Determination of hMPV RNA in lungs of infected mice by quantitative PCR. Total RNA from lungs of each animal sacrificed was obtained and used to produce cDNA by reverse transcription. Subsequently, the generated cDNA was used in a quantitative PCR reaction to determine the number of copies of viral RNA present in the sample relative to the number of copies of β-actin RNA. In FIG. 3A it can be observed that recombinant BCG vaccines for P (∗) and M2 (♦) proteins were protective of animal weight loss subsequent to infection, obtaining a weight similar to that of uninfected animals (▽) Moreover, unimmunized animals ( ) or immunized with Wild-type BCG (WT-BCG) (■), Live-hMPV ( ) or UV-hMPV ( ) suffered loss of animal body weight subsequent to infection. FIGS. 3B and 3C show that the recombinant BCG vaccine for P-protein prevented the infiltration of immune cells in the airways of animals following infection, obtaining an infiltration similar to uninfected animal. Moreover, unimmunized animals or animals immunized with Wild-type BCG, WT-BCG, Live-hMPV or UV-hMPV suffered post-infection immune cell infiltration in their airways. Vaccination with rBCG-M2 conferred incomplete protection. FIG. 3D shows that the number of hMPV virus expressed in N-hMPV gene copies per 5000 copies of β-actin present in lungs of infected unimmunized animals is similar to that of infected animals immunized with WT-BCG, Live-hMPV or UV-hMPV, that is, it would not provide protection, while infected animals immunized with rBCG-P-MPV virtually do not have the virus, as well as uninfected animals. Immunization with rBCG-M2 conferred an incomplete protection.

Figure 4:
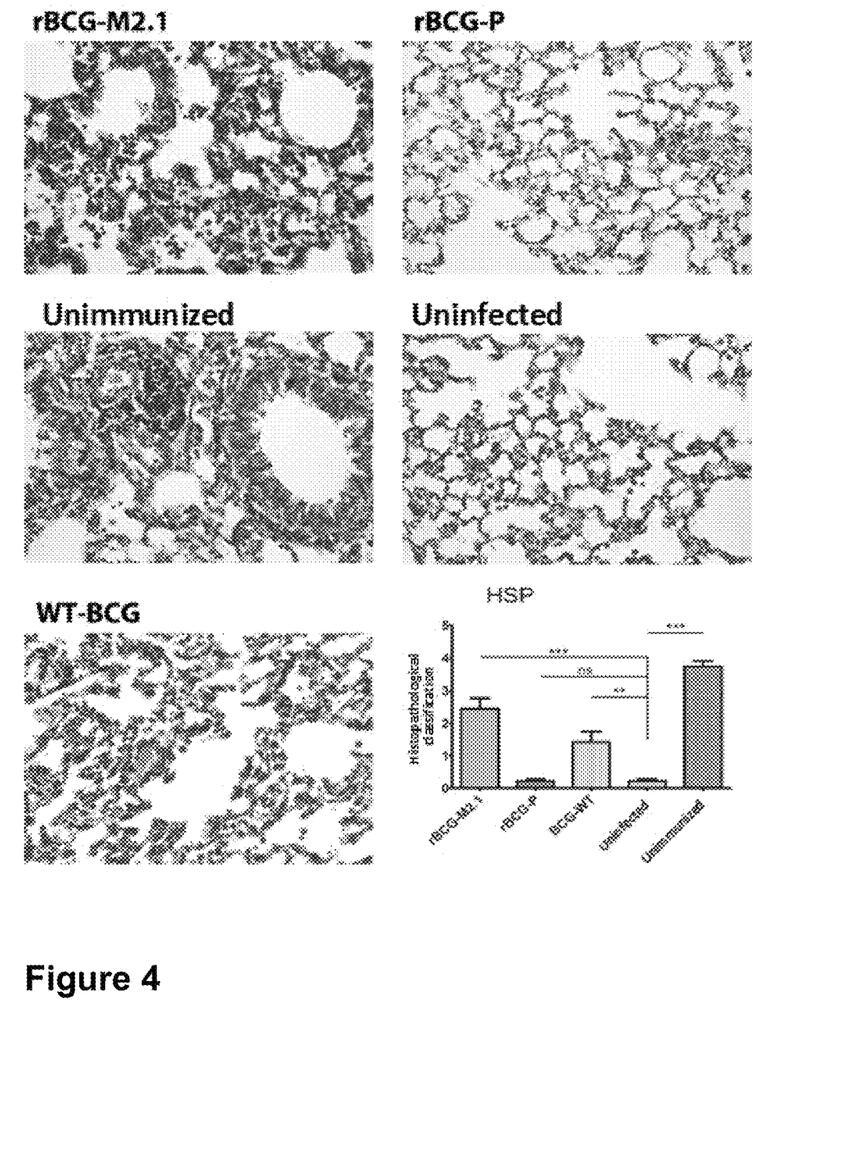
FIG. 4 shows samples of lungs from animals immunized with rBCG-M2.1-hMPV or WT-BCG and a quantification of inflammation score per group of animals (Histopathology Score).

FIG. 4 Immunization with rBCG-P-hMPV Protects Against Inflammation after Challenge with hMPV. The lungs of animals removed 6 days after challenge with $1 \times 10^6$ PFU of hMPV, were fixed in paraformaldehyde and embedded in paraffin and 7 μm sections were stained with hematoxylin and eosin. Significant infiltration of polymorph nuclear cells in unimmunized animals or animals immunized with rBCG-M2.1-hMPV or WT-BCG was observed. However, no signs of inflammation are observed in lungs obtained from animals immunized with rBCG-P-hMPV. Images are representative of six independent experiments. HSP represents quantification of inflammation score per group of animals (Histopathology Score). It can be appreciated that inflammation in animals immunized with rBCG-P-MPV and infected was very low or non-existent, similarly to the uninfected animals.

Figure 5:
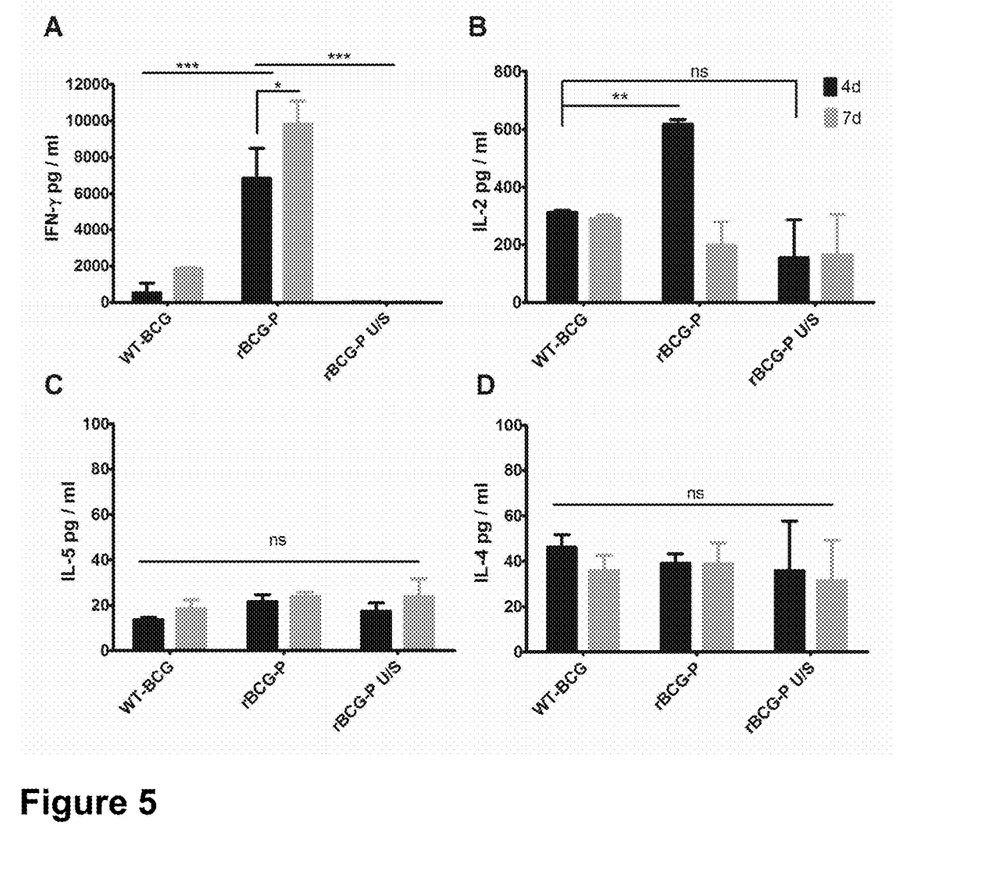
FIG. 5A shows supernatant of stimulated and non-stimulated rBCG-P-hMPV and WT-BCG spleen cells was analyzed by ELISA to determine levels of IFN-γ.
FIG. 5B shows supernatant of stimulated and non-stimulated rBCG-P-hMPV and WT-BCG spleen cells was analyzed by ELISA to determine levels of IL-2.
FIG. 5C shows supernatant of stimulated and non-stimulated rBCG-P-hMPV and WT-BCG spleen cells was analyzed by ELISA to determine levels of IL-5.
FIG. 5D shows supernatant of stimulated and non-stimulated rBCG-P-hMPV and WT-BCG spleen cells was analyzed by ELISA to determine levels of IL-4.

FIG. 5. Immunization with rBCG-P-hMPV Produces a Th1-Type Cytokine Profile. To determine the type of immune response responsible for rBCG-P-hMPV immunity, the cytokine profile of spleen cells of BALB/cj immunized with BCG strain recombinant for hMPV P-protein (rBCG-P-hMPV, in graphs: rBCG-P) was analyzed. Spleens of four BALB/cj immunized with rBCG-P-hMPV were recovered and spleen cells were stimulated during 7 days of incubation with 10 μg of P-protein-hMPV or PBS (U/S in graphs). As control, spleen cells of BALB/cj immunized with WT-BCG were cultured under the same conditions. The supernatant of stimulated and non-stimulated rBCG-P-hMPV and WT-BCG spleen cells was analyzed by ELISA to determine levels of (A) IFN-γ, (B) IL-2, (C) IL-5 and (D) IL-4 at days 4 and 7 of culture. Spleen cells derived from rBCG-P-hMPV stimulated with P-protein-hMPV (rBCG-P) secreted amounts significantly higher of IFN-γ compared with cells from animals immunized with WT-BCG or non-stimulated cells (rBCG-P U/S) (*** $p<0.001$, Student's t test), FIG. 5 A. Moreover, IFN-γ amounts increased between day 4-7 (* $p<0.05$, Student's t test), FIG. 5 A. Stimulated spleen cells from mice immunized with rBCG-P-hMPV (rBCG-P) produced significantly higher amounts of IL-2 at day 4 compared to non-stimulated cells (rBCG-P U/S) and basal level decreased at day 7 (**, $p<0.001$; ns=non-significant, Student's t test), FIG. 5 B. Spleen cells secreted low amounts of IL-5 and IL-4 without showing increase compared to spleen cells from WT-BCG o or non-stimulated (ns=non-significant, Student's t test), FIG. 5 C.

Figure 6:
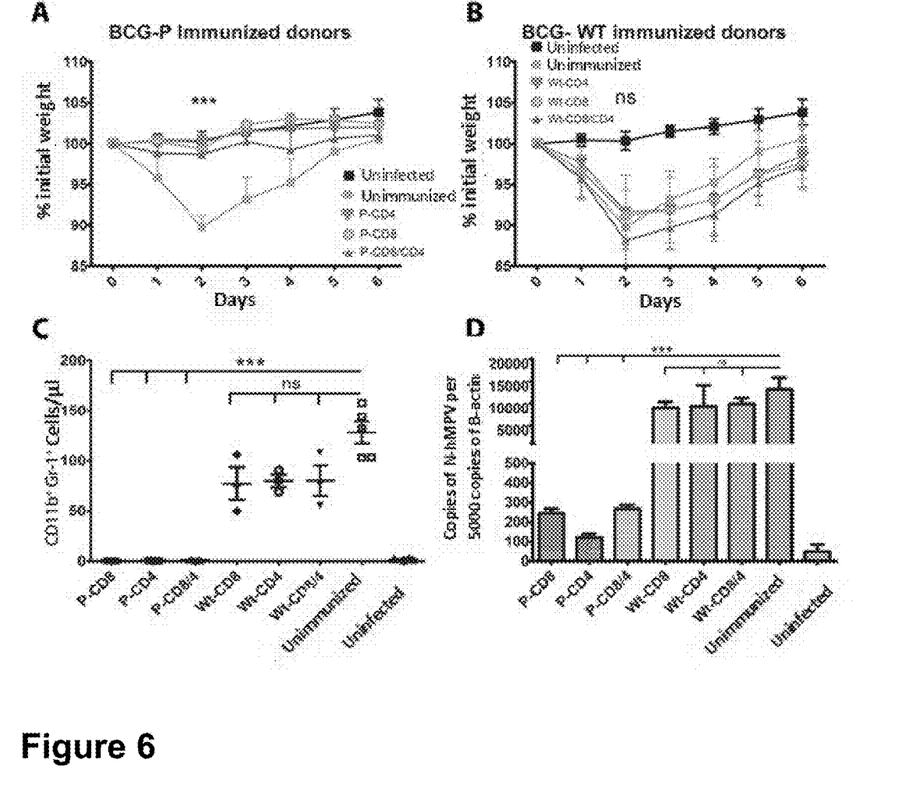
FIG. 6A shows mice transferred with $CD4^+$ and/or $CD8^+$ T lymphocytes from animals immunized with rBCG-P-MPV.
FIG. 6B shows T lymphocytes from animals immunized WT-BCG.
FIG. 6C shows bronchoalveolar lavage, BAL, from naïve mice previously transferred with $CD4^+$ and/or $CD8^+$ T lymphocytes from animals immunized with P-CD8, P-CD4, P-CD8/4.
FIG. 6D shows viral load in lungs of mice transferred with T lymphocytes (P-CD8, P-CD4, P-CD8/4) from mice immunized with rBCG-P-hMPV.

FIG. 6. Transfer of T Lymphocytes from mice immunized with rBCG-P-hMPV conferred resistance to hMPV infection in naïve mice. CD4+ T lymphocytes and CD8+ T cells were purified from splenocytes stimulated and non-stimulated with recombinant viral proteins. Independently, two million of stimulated or non-stimulated CD4+ or CD8+ T lymphocytes from animals immunized with rBCG-P-MPV or WT-BCG were transferred through the tail vein of naïve mice. Twenty-four hours after transfer, mice were intranasally infected with $1 \times 10^6$ PFU of hMPV. In FIG. 6A mice transferred with CD4+ and/or CD8+ T lymphocytes from animals immunized with rBCG-P-MPV showed no difference in body weight compared to uninfected mice. In contrast, we observed that mice transferred with CD4+ and/or CD8+ T lymphocytes from animals immunized WT-BCG lost significantly more weight after infection compared with uninfected animals ($p <0,0001$) (FIG. 6B). FIG. 6C shows that bronchoalveolar lavage, BAL, from naïve mice previously transferred with CD4+ and/or CD8+ T lymphocytes from animals immunized with (P-CD8, P-CD4, P-CD8/4), shows an infiltration significantly lower of granulocytes compared to mice transferred with T lymphocytes from WT-BCG (Wt-CD8, Wt-CD4, Wt-CD8/4) (* p <0,0001, Student's t test). Granulocyte infiltration in BAL of mice transferred with T lymphocytes from WT-BCG or not immunized mice does not show significant differences with infiltration of mice that received no T lymphocytes (NS=no significant, Student's t test). FIG. 6D shows that viral load in lungs of mice transferred with T lymphocytes (P-CD8, P-CD4, P-CD8/4) from mice immunized with rBCG-P-hMPV, was low compared to viral load of mice transferred with T lymphocytes (Wt-CD8, Wt-CD4, Wt-CD8/4) from animals immunized with WT-BCG strain and unimmunized animals (*, p <0,0001, Student's t test). The viral load in lungs of mice transferred with T lymphocytes from WT-BCG (Wt-CD8, Wt-CD4, Wt-CD8/4), shows no significant differences with unimmunized mice (ns=non-significant, Student's t test). Viral load was quantified as gene copies of N-hMPV by RT-qPCR, as described above.

DETAILED DESCRIPTION OF THE INVENTION

The present invention consists of an immunogenic formulation against hMPV comprising a recombinant BCG strain expressing the P-protein from human metapneumovirus. This formulation provides effective protection against infection by hMPV and does not generate inflammatory hyper-responsiveness.

The formulation of the invention may be delivered alone or mixed with other vaccines, such as an immunogenic formulation against SRV, in a mixed dose that would deliver protection against infection and/or complications associated with hMPV and SRV.

The immunogenic formulation detailed in this invention can be used to prepare vaccines containing live attenuated recombinant bacteria, from axenic cultures at doses between $1 \times 10^4$ CFU to $1 \times 10^{10}$ CFU per dose, especially dosages of $1 \times 10^8$ CFU per dose are preferred. The formulation will be presented lyophilized with a reconstituting solution which does not require an adjuvant because the adjuvant is the cell envelope composition of the recombinant bacteria. The lyophilized immunogenic formulation of the invention should be conserved between 4 and 8° C., protected from direct and indirect sunlight, presented in two separate vials, one containing the lyophilized recombinant bacteria and another with the reconstituent saline solution, to be mixed prior its administration.

Since its introduction in 1921, the vaccine based on *Mycobacterium bovis bacillus* Calmette-Guérin (BCG) has been used in more than one billion people and is currently used for tuberculosis worldwide.

The inventors have found that a way to shift the balance of immune response from a Th2-type pro-inflammatory response, whose protection is not stable in time, towards a Th1-type cell-based response, specifically $CD8^+$ cytotoxic T and $CD4^+$ helper T cells, is the use of adjuvants like the components of *Mycobacterium* cell wall. Specifically, expressing the immunogenic protein from hMPV in *Mycobacterium bovis bacillus* Calmette-Guérin (BCG).

F and G proteins from hMPV are found in the surface of the viral particle and therefore are accessible to circulating antibodies. Therefore, these proteins would be the obvious choice for a vaccine based on producing antibodies to prevent infection with hMPV.

Notwithstanding the foregoing, in the present invention we have chosen to use unexposed capsid proteins as immunogen, specifically P-protein, together with an adjuvant that promotes a Th1-type cell-based response, such as attenuated *Mycobacterium bovis* BCG bacteria. It has been found that capsid proteins as hMPV M2.1 promote the activation of cytotoxic lymphocytes (CTL). Surprisingly, in the present invention is described the use of the P-protein, a not-exposed protein from hMPV virus, which when used as immunogenic protein expressed by *Mycobacterium* allows to formulate an immunogenic composition, which when used as a vaccine or immunogenic composition provides effective protection without unwanted side effects such as inflammatory hyper-responsiveness.

The recombinant proteins expressed by the bacteria vector used herein are obtained by cloning genes encoding the same from group A hMPV virus in prokaryotic expression vectors, all commercially available. Metapneumovirus (hMPV) genome has been described previously and is available in GenBank database, Accession Number: AB503857.1, DQ843659.1, DQ843658.1, EF535506.1, GQ153651.1, AY297749.1, AY297748.1, AF371337.2, FJ168779.1, FJ168778.1, NC_004148.2 and AY525843.1. Obtaining the recombinant bacterial strain described herein includes heterologous expression of the viral proteins during bacterial replication in the host. Heterologous DNA sequences are integrated into the bacterial chromosomal DNA through expression vector pMV361. These hMPV proteins may be genetically engineered, such as by incorporation of peptide sequences or glycosylation domains and/or subsequent destination to endocytic or phagocytic receptors of antigen presenting cells by their coupling to natural ligands using the biotin-streptavidin system (using commercial biotinylation kits and genetic modification of viral proteins by coupling to bacterial protein streptavidin, or by introducing the genetic sequence encoding for amino acid sequences described as biotinylation signals in recombinant proteins or protein fragments, using techniques previously described for prokaryotic and/or eukaryotic heterologous expression systems).

Immunogenic formulation of the invention comprises the expression of hMPV P-protein either complete or an immunogenic fragment thereof, in an attenuated strain of *Mycobacterium*. Especially preferred is the recombinant attenuated *Mycobacterium* strain derived from *Bacillus* Calmette-Guérin (BCG) strain. HMPV P-protein can be P-protein from Metapneumovirus subtypes A or B.

The recombinant attenuated *Mycobacterium* strain of the invention can contain nucleic acid sequences encoding for hMPV P-protein or an immunogenic fragment thereof inserted into the bacterial genome or into an extrachromosomal plasmid, in one or more copies. The protein expression can be under the control of constitutive or inducible, endogenous or exogenous promoters from *Mycobacterium* BCG.

The HMPV P-protein or an immunogenic fragment thereof can be expressed in soluble, soluble-cytoplasmic form, as extracellularlly secreted or membrane-bound protein. The immunogenic formulation of the invention may comprise two or more recombinant attenuated strains of *Mycobacterium*, wherein the proteins or immunogenic fragments of hMPV P-protein from the strains are expressed to generate a different number of copies, are constitutively or inducible expressed, and/or are located in different cellular locations.

The immunogenic formulation disclosed herein can be used in conjunction with other immunogenic formulations comprising further antigen formulations against different virus of hSRV and hMPV, with attenuated strains of BCG and seasonal vaccines against influenza A and B.

The above described immunogenic formulation can be applied to individual in subcutaneous/subdermal form in conjunction with a buffered saline (PBS, sodium phosphate buffer) or saline solution.

To develop the recombinant *Mycobacterium* bacteria expressing hMPV P-protein, first we must generate a vector expressing said protein. Any known mycobacterial expression vector can be used, and the gene encoding for the P-protein from hMPV virus must be inserted in phase with its promoter region. In a preferred embodiment, a reverse transcription with universal primers from the RNA from isolated human metapneumovirus is performed. Subsequently the P-protein gene is amplified with specific primers (FIG. 1A). The amplification product is inserted into the expression vector. In the present invention we have used the mycobacterial expression vector pMV361, generating the vector pMV361-P-hMPV (FIG. 1B).

The vector, once obtained, is used to transform a *Mycobacterium* strain, such as *Mycobacterium* BCG. For the purposes of the invention any known BCG strain can be used, such as BCG Pasteur or BCG Danish. The method of transformation can be any method available, especially preferred is electrotransformation. Subsequently, the transformed cells expressing hMPV P-protein must be selected.

These recombinant cells are the immunogenic formulation of the invention, which is provided in amounts from between $10^4$ to $10^9$ CFU/dose in a pharmacologically appropriate saline buffer.

In addition, the formulation of the invention can be formulated in combination with recombinant BCG strains expressing immunogenic proteins from respiratory syncytial virus (RSV). In a preferred embodiment, the recombinant BCG bacteria expressing the hMPV P-protein is provided in conjunction with recombinant BCG bacteria expressing N, P, M, F, M2 (ORF1 and 2), SH, G or L proteins from SRV. In a more preferred embodiment, the immunogenic formulation of the invention is used in combination with a BCG strain recombinant for N gene from RSV. Particularly, the combination of BCG recombinant for the P gene from hMPV subtype A and BCG recombinant for the N gene of RSV subtype A is preferred.

In another embodiment of the invention a BCG strain is transformed with a vector expressing the hMPV P-protein and then the transformed cell is re-transformed with a vector expressing a protein of respiratory syncytial virus (RSV). RSV protein is selected from N, P, M, F, M2 (ORF1 and 2), SH, G or L. Particularly is firstly preferred a transformation with a vector expressing the P-protein from hMPV subtype A, and secondly subjecting these transformed strains to a second transformation with a vector expressing the N gene of RSV subtype A, obtaining a BCG strain simultaneously expressing P-protein from hMPV subtype A and N-protein from SRV subtype A.

The immunogenic formulation of the invention can be provided lyophilized in a multidose presentation ready for reconstitution in 1 ml of an attached saline solution to obtain $1 \times 10^9$ CFU/ml of reconstituted solution. Each 0.1 ml of resuspended solution will contain the appropriate dose of $1 \times 10^8$ CFU for administration.

To prepare the lyophilized solution transformed strains of the invention can be suspended in any appropriate lyophilization solution, for example LYO C buffer comprising 4% (w/v) mannitol, 0.05% (w/v) Tyloxapol, 0.25% sucrose and 5 mM histidine can be used. Then it can be lyophilized and conserved at 25° C.

The reconstituent solution can be any available in the art, in one embodiment a dilute Sauton SSI solution (125 µg MgSO$_4$, 125 µg K$_2$HPO$_4$, 1 mg L- asparagine, 12.5 µg ferric ammonium citrate, 18.4 mg 85% glycerol, 0.5 mg citric acid in 1 ml H2O) at −80° C. is preferred. In another embodiment, the formulation of the invention can be suspended in PBS (137 mM NaCl; 2.7 mM KCl; 4.3 mM Na2HPO4; 1.47 mM KH2PO4, pH 7,4), supplemented with 20% Glycerol, 0.02% TWEEN® 80 (Polyoxyethylene (20) sorbitan monooleate) at a final concentration of $10^8$ bacteria per 100 µl and conserved at −80° C. Both in the presence of a nonionic detergent such as 0.1% TWEEN® 80 (Polyoxyethylene (20) sorbitan monooleate) or 0.05% Tyloxapol.

The formulation of the invention should be kept between 4-8° C. before and after reconstitution, kept away from direct and indirect sunlight all the time and upon reconstitution it should be discarded at the end of the day.

The following examples for generating and using the immunogenic formulation against hMPV based on the recombinant *Mycobacterium* bacteria expressing viral proteins are illustrative only and are not intended to limit the production or application scope of the invention. Although specific terms are used in the following descriptions, its use is only descriptive and not limiting.

EXAMPLES

Example I

Generation of a Recombinant Vector Allowing the Expression of the hMPV P-protein in *Mycobacterium* BCG The coding region of metapneumovirus P gene was amplified from RNA using the following primers: P-hMPV_Fw: GAATTCATGTCATTCCCTGAAGGAAA (SEQ ID No 1) and P-hMPV_Rv: GAATTCCTACATAATTAACTGG-TAAA (SEQ ID No 2), where the underlined sequences incorporate the EcoRI site at both ends of the amplification product, FIG. 1A. Mycobacterial vector pMV361 was linearized into the EcoRI site, allowing to insert the sequence corresponding to the P gene from hMPV:

```
                                              (SEQ ID No 3)
GAATTCATGTCATTCCCTGAAGGAAAAGATATTCTTTTCATGGGTAATG

AAGCGGCAAAATTGGCAGAAGCTTTCCAAAAATCATTAAGAAAACCTAG

TCATAAAAGATCTCAATCTATTATAGGAGAAAAAGTGAACACTGTATCT

GAAACATTGGAATTACCTACTATCAGTAGACCTACCAAACCGACCATAT

TGTCAGAGCCGAAGTTAGCATGGACAGACAAAGGTGGGCAATCAAAAC

TGAAGCAAAGCAAACAATCAAAGTTATGGATCCTATTGAAGAAGAAGAG

TTTACTGAGAAAAGGGTGCTGCCCTCCAGTGATGGGAAAACTCCTGCAG

AAAAGAAGTTGAAACCATCAACCAATACTAAAAAGAAGGTCTCATTTAC

ACCAAATGAACCAGGAAAATACACAAAGTTGGAGAAAGATGCTCTAGAC

TTGCTTTCAGACAATGAAGAAGAAGATGCAGAATCCTCAATCTTAACCT

TCGAAGAAAGAGATACTTCATCATTAAGCATTGAAGCCAGACTAGAATC

GATTGAGGAGAAATTAAGCATGATATTAGGGCTATTAAGAACACTCAAC

ATTGCTACAGCAGGACCCACAGCAGCAAGAGATGGGATCAGAGATGCAA
```

-continued

```
TGATTGGCATAAGGGAGGAACTAATAGCAGACATAATAAAAGAAGCCAA

GGGAAAAGCAGCAGAAATGATGGAAGAAGAAATGAACCAGCGGACAAAA

ATAGGAAACGGTAGTGTAAAATTAACTGAAAAGGCAAAGGAGCTCAACA

AAATTGTTGAAGACGAGAGCACAAGTGGTGAATCCGAAGAAGAAGAAGA

ACTAAAAGACACACAGGAAAATAATCAAGAAGATGACATTTACCAGTTA

ATTATGTAGGAATTC
```

The insertion of the open-frame of hMPV P gene into the EcoRI site of the vector pMV361 locates it under control of the hsp60 promoter and led to the construction of pMV361-P-hMPV (FIG. 1B).

Example II

Immunogenic Formulation Comprising 10 Doses of $1 \times 10^8$ CFU Each of BCG Danish Strain Recombinant for the P Gene from hMPV Subtype A The P gene from hMPV subtype A is inserted in one copy into the bacterial genome under regulation of endogenous constitutive hsp 60 promoter from *Mycobacterium* BCG for protein expression.

The Mycobacterium BCG Danish strain (ATCC 35733) was transformed by electrotransformation with the plasmid pMV361-P-hMPV, derived from plasmid pMV361 (Stover et al., 1991), which is inserted once in the bacterial genome. This plasmid contains the gene encoding for the P-protein from hMPV subtype A, which is expressed under the endogenous constitutive promoter of gene hsp60 from BCG. The resulting recombinant colonies were grown (at 37° C. in supplemented Middlebrock 7H9 culture medium (4.9 g/L)) up to $OD_{600nm}=1$, centrifuged at 4000 rpm for 20 min (Eppendorf rotor model 5702/R A-4-38) and resuspended in PBS (137 mM NaCl, 2.7 mM KCl, 4.3 mM $Na_2HPO_4$, 1.47 mM $KH_2PO_4$, pH 7.4) supplemented with 20% glycerol and 0.02% TWEEN® 80 (Polyoxyethylene (20) sorbitan monooleate) up to a final concentration of $10^8$ bacteria per 100 µl and conserved at −80° C.

Similarly, the strains can be resuspended in a volume solution: 25% lactose volume and Proskauer and Beck Medium supplemented with glucose and TWEEN® 80 (Polyoxyethylene (20) sorbitan monooleate) (PBGT: 0.5 g asparagine, 5.0 g monopotassium phosphate, 1.5 g citrate magnesium, 0.5 g potassium sulfate, 0.5 ml TWEEN® 80 (Polyoxyethylene (20) sorbitan monooleate) and 10.0 g glucose per liter of distilled water) to be lyophilized and then conserved at 25° C.

Using Western blot and antibodies for the hMPV P-protein, it can be seen that this strain of BCG constitutively expressed P-protein from hMPV subtype A in the cytoplasm (FIG. 2A). Immunization of BALB/c mice with a subdermal dose of $1 \times 10^6$ colony forming units (CFU) of rBCG-P-hMPV, as a vaccine, confers protection to these animals against intranasal infection with $10^6$ plaque forming units of hMPV subtype A (FIG. 3). The effect of the vaccine of the invention, rBCG-P-hMPV, was compared with a rBCG vaccine expressing another protein from hMPV, M2 protein, and with untransformed BCG; an unimmunized group was used as control, all groups were intranasally infected with hMPV, an unimmunized, uninfected control was also included. The variation in weight of animals after infection was analyzed, the results are shown in FIG. 3A. Both recombinant BCG vaccines for P (•) and M2 (♦) proteins from hMPV were protective of weight loss subsequent to animal infection, obtaining a weight similar to uninfected animal (▼). Moreover, unimmunized animals (•) or animals immunized with Wild-type BCG (WT-BCG) (■), Live-hMPV (•) or UV-hMPV (•) suffered loss of body weight post-infection.

Immune cell infiltration in the airways of animals after infection was also analyzed, which is an indicative parameter of disease development. This was analyzed by the number of infiltrated cells into the airway (FIG. 3B) and through infiltrating cells that being positive for CD11b and Gr1 correspond to granulocytes (FIG. 3C). FIG. 3b shows that only the vaccine of the invention rBCG-P-hMPV prevented lymphocyte infiltration in airways, resulting in an infiltration similar to uninfected animals. Moreover, animals unimmunized or immunized with Wild-type BCG (WT-BCG) or rBCG-M2-hMPV vaccines suffered infiltration of immune cells in airways post-infection. Vaccination with rBCG-M2 conferred incomplete protection in animal airways for immune cells infiltration.

Additionally, a number of copies of the N-hMPV gene RNA in lung cells of different groups under study was analyzed. A greater number of copies of the hMPV virus RNA is indicative of greater infection, the results are normalized per β-actin copies. The results are shown in FIG. 3D. It is appreciated that the number of hMPV virus present in the lungs of unimmunized infected animals is similar to that of infected animals immunized with WT-BCG, Live-hMPV or UV-hMPV, i.e., these immunizations would not confer protection. It is observed that immunization with rBCG-M2 conferred an incomplete protection. In addition, practically there is no virus in infected animals immunized with the vaccine of the invention rBCG-P, with results similar to the group of uninfected animals. This proves that the formulation of the invention effectively protects against infection with hMPV.

Example III

Immunogenic Formulation Comprising $5 \times 10^7$ Bacteria from *Mycobacterium* BCG Danish Strain Recombinant for the P Gene from hMPV Subtype a and $5 \times 10^7$ Bacteria from *Mycobacterium* BCG Danish Strain Recombinant for the N Gene from RSV Subtype A In each bacteria composing the immunogenic formulation, the genes from hMPV and RSV are inserted into the bacterial genome in one copy under regulation of the endogenous constitutive hsp60 promoter from BCG and protein expression is cytoplasmic. The immunogenic formulation is preserved in PBS (137 mM NaCl, 2.7 mM KCl, 4.3 mM $Na_2HPO_4$, 1.47 mM $KH_2PO_4$, pH 7.4) supplemented with 20% glycerol and 0.02% TWEEN® 80 (Polyoxyethylene (20) sorbitan monooleate)at a final concentration of $10^8$ bacteria per 100 µl and conserved at −20° C.

BCG Danish strains (ATCC 35733) were transformed by electrotransformation with plasmid pMV361-P from hMPV to give the strain of the invention rBCG-P-MPV, and additionally a second group was transformed with pMV361-N from SRV to obtain the transformed strain rBCG-N SRV, these plasmids are derived from plasmid pMV361 (Stover et al., 1991), which are inserted into the bacterial genome once. The resulting recombinant colonies were grown at 37° C. in a supplemented Middlebrock 7H9 culture medium up to OD$_{600\ nm}$=1, centrifuged at 4000 rpm for 20 min (Eppendorf rotor model 5702/R A-4-38) and resuspended in PBS (137 mM NaCl, 2.7 mM KCl, 4.3 mM Na$_2$HPO$_4$, 1.47 mM KH$_2$PO$_4$, pH 7.4) supplemented with 20% glycerol and 0.02% TWEEN® 80 (Polyoxyethylene (20) sorbitan monooleate) up to a final concentration of 10$^7$ bacteria per 100 µl and conserved at −20° C. Strains were resuspended in LYO C buffer, comprising 4% (w/v) mannitol, 0.05% (w/v) Tyloxapol, 0.25% sucrose and 5 mM histidine, then lyophilized and conserved at 4° C. Using Western blot analysis and specific antibodies for the hMPV P-protein or RSV N-protein, it was observed that BCG Danish strains recombinantly expressed, P-protein from hMPV or N-protein from SRV, subtype A, respectively (FIG. 2). An immunogenic formulation comprising both transformed strains simultaneously conferred immunity against hMPV and RSV virus.

Example IV

Immunogenic Formulation of $10^4$ Bacteria from BCG Danish Strain Recombinant for the P Gene from hMPV Subtype A A BCG Danish strain was transformed with the P gene from hMPV subtype A, so that the gene was inserted into the bacterial genome in one copy under the regulation of the endogenous inducible acr promoter from BCG, which is active in response to nitric oxide, low oxygen concentrations, and stationary growth phases. Protein expression is cytoplasmic. The immunogenic formulation was lyophilized in LYO C buffer, comprising 4% (w/v) mannitol 0.05% (w/v) Tyloxapol, 0.25% sucrose and 5 mM histidine and was conserved reconstituted at 25° C. in dilute Sauton SSI solution (125 μg $MgSO_4$, 125 μg $K_2HPO_4$, 1 mg L-asparagine, 12.5 μg ferric ammonium citrate, 18.4 mg 85% glycerol, 0.5 mg citric acid in 1 ml $H_2O$). Alternatively, the transformed strains can be preserved in PBS (137 mM NaCl; 2.7 mM KCl; 4.3 mM $Na_2HPO_4$; 1.47 mM $KH_2PO_4$, pH 7,4) supplemented with 0.02% TWEEN® 80 (Polyoxyethylene (20) sorbitan monooleate) and 20% glycerol up to a final concentration of $10^4$ bacteria per 100 μl.

BCG Danish strain (American Type Culture Collection, www.atcc.org, ATCC number 35733) was transformed by electrotransformation with the plasmid $pMV361_{Pacr}$/P-hMPV derived from the plasmid pMV361 (Stover et al., 1991), which is inserted into the bacterial genome once. This plasmid contains the gene encoding for the P-protein from hMPV subtype A, which is expressed under the endogenous inducible acr promoter from BCG. The resulting recombinant colonies were grown (at 37° C. supplemented Middlebrock 7H9 culture medium) up to $OD_{600\ nm}$=1, centrifuged at 4000 rpm for 20 min (Eppendorf rotor model 5702/R A-4-38) and resuspended in a LYO C buffer solution, composed of 4% (w/v) mannitol, 0.05% (w/v) Tyloxapol, 0.25% sucrose and 5 mM histidine. Finally, 1 ml aliquots with $10^4$ bacteria were lyophilized and conserved at 25° C. Similarly, the strains can be preserved in PBS (137 mM NaCl; 2.7 mM KCl; 4.3 mM $Na_2HPO_4$; 1.47 mM $KH_2PO_4$, pH 7,4) supplemented with 0.02% TWEEN® 80 (Polyoxyethylene (20) sorbitan monooleate) and 20% glycerol at a final concentration of $10^4$ bacteria per 100 μl. This immunogenic formulation confers immunity against hMPV virus.

Example V

Immunogenic Formulation Consisting of $10^9$ Bacteria from BCG Danish Strain Recombinant for the Gene P from hMPV Subtype A The gene is inserted into the bacterial genome in one copy, under regulation of the exogenous T7-phage promoter for constitutive expression in BCG strains that co-express T7-phage polymerase. Protein expression is cytoplasmic. The immunogenic formulation is suspended in dilute Sauton SSI solution (125 μg $MgSO_4$, 125 μg $K_2HPO_4$, 1 mg L-asparagine, 12.5 μg ferric ammonia citrate, 18.4 mg 85% glycerol, 0.5 mg citric acid in 1 ml H2O) and was conserved at 20° C., or can be lyophilized and conserved at 4° C. Similarly, the strains can be preserved in PBS (137 mM NaCl; 2.7 mM KCl; 4.3 mM $Na_2HPO_4$; 1.47 mM $KH_2PO_4$, pH 7.4) supplemented with 0.02% TWEEN® 80 (Polyoxyethylene (20) sorbitan monooleate) and 20% glycerol up to a final concentration of $10^9$ bacteria per 100 μl.

The BCG Danish strain ATCC 35733 was transformed by electrotransformation with the plasmid $pMV361_{pT7}$/P-hMPV derived from the plasmid pMV361 (Stover et al., 1991), which is inserted into the bacterial genome once. This plasmid contains the gene encoding the P-protein from hMPV subtype A, which is expressed under T7 promoter activated by the expression of the T7-phage polymerase.

The resulting BCG strain was transformed by electrotransformation with the plasmid $pMV261_{Amp}$/PolT7 derived from the plasmid pMV261 (Stover et al., 1991), which resides extrachromosomally in multiple copies inside the bacteria. In this plasmid, the resistance against the antibiotic kanamycin has been replaced by resistance against antibiotic hygromycin (Hygr). The T7 polymerase from the T7 phage is under control of the constitutive promoter of the hsp60 gene from BCG. The resulting recombinant colonies were grown at 37° C. in supplemented Middlebrook 7H9 culture medium up to $OD_{600\ nm}$=1, centrifuged at 4000 rpm for 20 min (Eppendorf rotor model 5702/R A-4-38) and resuspended in dilute Sauton SSI solution (125 μg $MgSO_4$, 125 μg $K_2HPO_4$, 1 mg L-asparagine, 12.5 μg ferric ammonium citrate, 18.4 mg 85% glycerol, 0.5 mg citric acid in 1 ml $H_2O$)) and conserved at −80° C. This immunogenic formulation confers immunity against hMPV virus.

Example VI

Inoculation of $10^8$ Bacteria from BCG Danish Strain Recombinant for hMPV-P Gene in any of the Immunogenic Formulation Thereof Protects from Immunopathological Damage Inoculation of the recombinant BCG strain expressing the P-protein from metapneumovirus in any of its formulations protects against clinical signs and symptoms of infection with strain A and B of hMPV. Decreases anorexia caused by fever and malaise (FIG. 3A), as well as the infiltration of the airways (FIGS. 3B 3C). It also decreases the replication and spread of strains A and B of hMPV (FIG. 3D).

Inoculation of the formulation in any presentation also significantly reduces histopathological manifestations of infection by strains A and B of hMPV. The lungs of animals immunized with the formulation show a much less infiltration of immune cells, loss of structure and inflammation of lung tissue with respect to unimmunized animals or animals immunized with the wild-type strain (FIG. 4).

Inoculation of the formulation with the recombinant BCG expressing the hMPV P-protein in any presentation generates a cell-based immunity that can be transferred to naïve individuals by recovery and purification of T lymphocytes from immunized donors (FIG. 6).

The above examples are extended to immune formulations containing a recombinant attenuated *Mycobacterium* strain expressing hMPV P-protein or a substantial part of the same, as well as all combinations with immunological formulations containing a recombinant attenuated *Mycobacterium* strain expressing any of NS2, N, P, M, SH, M2 (ORF1), M2 (ORF2), L, F or G proteins from RSV. Also examples are extended to immunological formulations which contain one or several recombinant attenuated *Mycobacterium* strains; wherein said recombinant bacteria contains protein genes, or immunogenic fragments of the hMPV P-protein embedded in either the bacterial genome or extra-chromosomal plasmids, in one or more copies, and the expression thereof is commanded by endogenous or exogenous, constitutive or inducible promoters, and it is expressed in a cytoplasmic-soluble form extracellularly secreted or as cell membrane-bound proteins.

REFERENCES

Biacchesi, S., Pham, Q. N., Skiadopoulos, M. H., Murphy, B. R., Collins, P. L. & Buchholz, U. J. (2005). Infection of nonhuman primates with recombinant human metapneumovirus lacking the SH, G, or M2-2 protein categorizes each as a nonessential accessory protein and identifies vaccine candidates. *J Virol* 79, 12608-12613.

Cseke, G., Wright, D. W., Tollefson, S. J., Johnson, J. E., Crowe, J. E., Jr. & Williams, J. V. (2007). Human metapneumovirus fusion protein vaccines that are immunogenic and protective in cotton rats. *J Virol* 81, 698-707.

Denis, F., Alain, S., Hantz, S. & Lagrange, P. (2005). [Antiviral vaccination and respiratory mucosal immunity: still disappointing results from a seductive idea]. *Presse Med* 34, 1245-1253.

Hamelin, M. E., Couture, C., Sackett, M., Kiener, P., Suzich, J., Ulbrandt, N. & Boivin, G. (2008). The prophylactic administration of a monoclonal antibody against human metapneumovirus attenuates viral disease and airways hyperresponsiveness in mice. *Antivir Ther* 13, 39-46.

Herist, S., de Graaf, M., Schrauwen, E. J., Sprong, L., Hussain, K., van den Hoogen, B. G., Osterhaus, A. D. & Fouchier, R. A. (2008a). Generation of temperature-sensitive human metapneumovirus strains that provide protective immunity in hamsters. *J Gen Virol* 89, 1553-1562.

Herist, S., Schrauwen, E. J., de Graaf, M., van Amerongen, G., van den Hoogen, B. G., de Swart, R. L., Osterhaus, A. D. & Fouchier, R. A. (2008b). Immunogenicity and efficacy of two candidate human metapneumovirus vaccines in cynomolgus macaques. *Vaccine* 26, 4224-4230.

Karron, R. A., Wright, P. F., Belshe, R. B. & other authors (2005). Identification of a recombinant live attenuated respiratory syncytial virus vaccine candidate that is highly attenuated in infants. *J Infect Dis* 191, 1093-1104.

Kolli, D., Bataki, E. L., Spetch, L., Guerrero-Plata, A., Jewell, A. M., Piedra, P. A., Milligan, G. N., Garofalo, R. P. & Casola, A. (2008). T lymphocytes contribute to antiviral immunity and pathogenesis in experimental human metapneumovirus infection. *J Virol* 82, 8560-8569.

Stover, C. K., de la Cruz, V. F., Fuerst, T. R. & other authors (1991). New use of BCG for recombinant vaccines. *Nature* 351, 456-460.

Yim, K. C., Cragin, R. P., Boukhvalova, M. S., Blanco, J. C., Hamlin, M. E., Boivin, G., Porter, D. D. & Prince, G. A. (2007). Human metapneumovirus: enhanced pulmonary disease in cotton rats immunized with formalin-inactivated virus vaccine and challenged. *Vaccine* 25, 5034-5040.

The invention claimed is:

1. An immunogenic formulation that confers protection against infection by human metapneumovirus (hMPV) and/or attenuates the pathogenicity of the hMPV, wherein the formulation comprises one or more recombinant attenuated *Mycobacterium* strain in an amount that ranges from $10^4$ to $10^9$ bacteria CFU/dose per strain, wherein each strain expresses an hMPV P-protein or an immunogenic fragment thereof in a pharmacologically appropriate saline buffer.

2. The immunogenic formulation according to claim 1, wherein the recombinant attenuated *Mycobacterium* strain is derived from *Bacillus* Calmette-Guérin (BCG) strain.

3. The immunogenic formulation according to claim 1, wherein the hMPV P protein is subtype A or subtype B.

4. The immunogenic formulation according to claim 1, wherein the nucleic acid sequence encoding the hMPV P-protein or the immunogenic fragment thereof is inserted into the genome of an attenuated strain of *Mycobacterium* or into a extrachromosomal plasmid, in one or more copies of plasmid, so that the viral protein or immunogenic fragment is expressed from the nucleic acid sequence.

5. The immunogenic formulation according to claim 1, wherein the formulation comprises two or more recombinant attenuated *Mycobacterium* strains, wherein each of the strains expresses the hMPV P-protein or the immunogenic fragment thereof in a different location, as a soluble, cytoplasmic-soluble, extracellularly secreted or membrane-bound protein.

6. The immunogenic formulation according to claim 1, wherein the hMPV proteins or the immunogenic fragment thereof is derived from the expression of nucleic acid under the control of constitutive or inducible, endogenous or exogenous promoters from *Mycobacterium* BCG strain.

7. The immunogenic formulation of claim 1, wherein said formulation comprises two or more recombinant attenuated *Mycobacterium* strains, wherein the hMPV protein or immunogenic fragment thereof from the *Mycobacterium* BCG strain is expressed to generate a different number of copies, is constitutively or inducible expressed, and/or is located in different cellular locations.

8. The immunogenic formulation according to claim 1, wherein the protein or immunogenic fragment thereof is expressed as soluble cytoplasmic protein, secreted extracellularly, or cell membrane-bound.

9. A method for protection against hMPV infection or disease caused by hMPV, comprising administering to a subject in need thereof the immunogenic composition of claim 1.

10. The method of claim 9, wherein said formulation is administered subcutaneously, percutaneously or subdermally.

11. A lyophilized or freeze-dried formulation comprising one or more recombinant attenuated *Mycobacterium* strain in an amount that ranges from $10^4$ to $10^9$ bacteria CFU/dose per strain, wherein each strain expresses a hMPV protein or an immunogenic fragment thereof.

12. The lyophilized or freeze-dried formulation according to claim 11, wherein the recombinant attenuated *Mycobacterium* strain is derived from *Bacillus* Calmette-Guerin (BCG) strain.

13. The lyophilized or freeze-dried formulation according to claim 11, wherein the hMPV protein is subtype A or subtype B.

* * * * *